United States Patent [19]
Longsworth

[11] Patent Number: 5,452,582
[45] Date of Patent: Sep. 26, 1995

[54] CRYO-PROBE

[75] Inventor: Ralph C. Longsworth, Allentown, Pa.

[73] Assignee: APD Cryogenics, Inc., Allentown, Pa.

[21] Appl. No.: 271,102

[22] Filed: Jul. 6, 1994

[51] Int. Cl.$^6$ .............................. F25B 19/02; F25D 3/00
[52] U.S. Cl. ................. 62/51.2; 62/293; 606/24; 606/25
[58] Field of Search .............. 62/51.2, 293; 606/24

[56] References Cited

U.S. PATENT DOCUMENTS

| | | | |
|---|---|---|---|
| 3,782,386 | 1/1974 | Barger | 62/293 X |
| 3,800,552 | 4/1974 | Sollami et al. | 62/293 |
| 3,993,075 | 11/1976 | Lisenbee et al. | 62/293 X |
| 4,018,227 | 4/1977 | Wallach | 62/293 X |
| 4,146,030 | 3/1979 | Holroyd | 62/293 X |
| 4,178,775 | 12/1979 | Smetana | 62/51.2 |
| 4,275,734 | 6/1981 | Mitchiner | 62/51.2 X |
| 4,278,090 | 7/1981 | Van Gerven | 62/51.2 X |
| 4,377,168 | 3/1983 | Rzasa et al. | 606/24 |
| 5,108,390 | 4/1992 | Potocky et al. | 606/24 X |

FOREIGN PATENT DOCUMENTS

| | | | |
|---|---|---|---|
| 2093964 | 9/1982 | United Kingdom | 62/51.2 |

*Primary Examiner*—Christopher Kilner
*Attorney, Agent, or Firm*—Helfgott & Karas

[57] ABSTRACT

In the cryo-probe, refrigerant is furnished from a high pressure, room temperature supply. Insulation of the refrigerant lines is unnecessary. Refrigerant flows through a pre-cooling heat exchanger in the probe and through a restrictor wherein the pressure drops. In accordance with the Joule-Thompson effect, the refrigerant expands and becomes cold and liquid is applied in the region of the cryo-tip to provide rapid cooling thereof. Expanded refrigerant gas at low pressure reverses direction and flows back from the cold tip in counterflow arrangement through the aforementioned heat exchanger to give a pre-cooling effect to the refrigerant incoming from the external supply. A second tube for conveying warm-up gas is located in the probe and extends to the cold tip. After cryosurgery is complete, the high pressure flow is stopped and warm gas is delivered to the tip in the probe at reduced pressure through the second tube from the same refrigerant supply as is used for cooling. Accordingly, the tip is rapidly warmed.

14 Claims, 5 Drawing Sheets

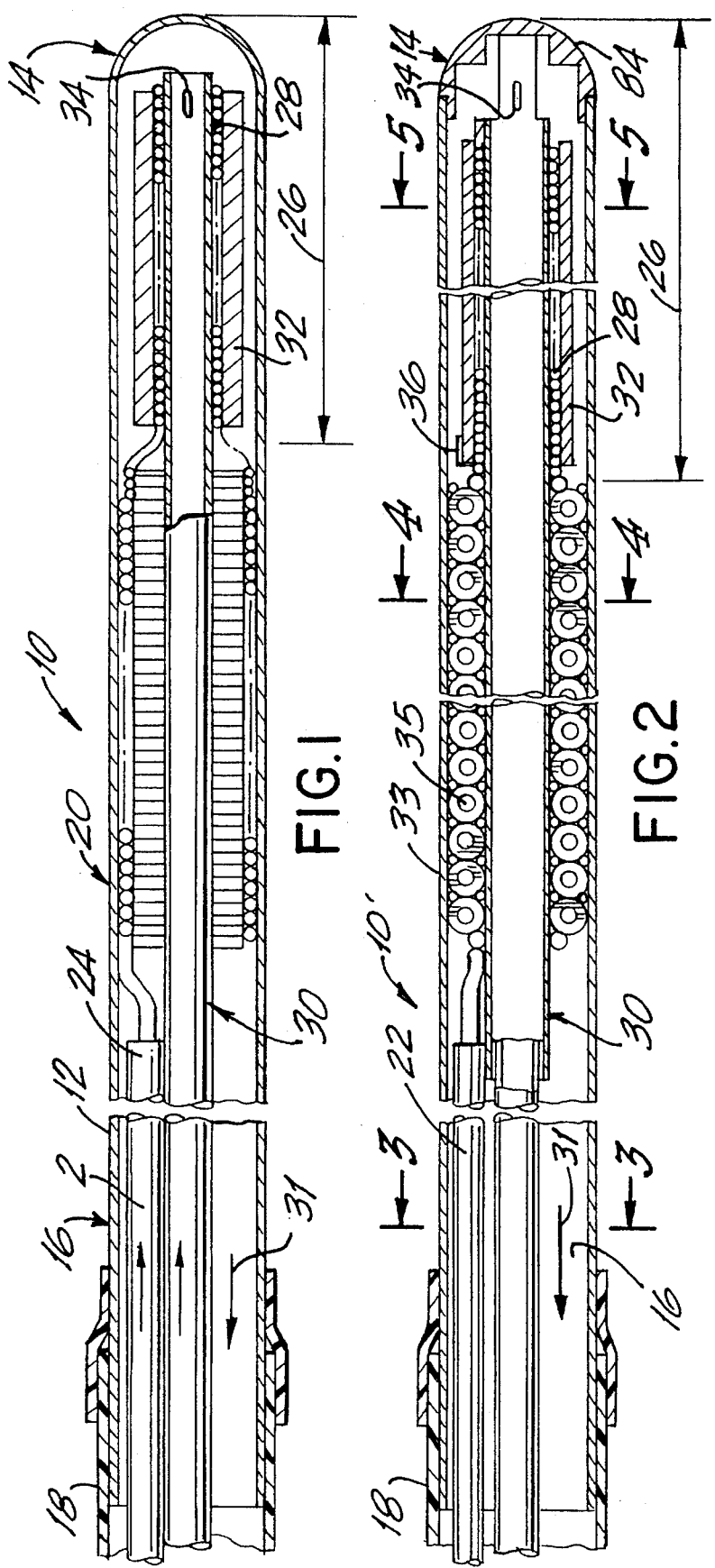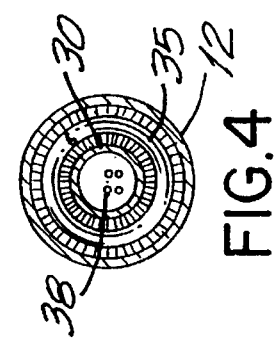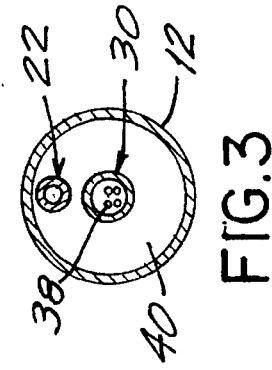

CRYO-PROBE

BACKGROUND OF THE INVENTION

The present invention relates to cryosurgical probes, and more particularly to a cryo-probe construction that provides rapid defrost of an ice ball that is formed during use of the probe for cell necrosis. Cryosurgical probes have been built that use direct expansion of liquid refrigerant R12, carbon dioxide, nitrous oxide and other materials having two phase characteristics in a desired temperature range. The mentioned materials, stored at room temperature can produce temperatures in a range from −29° C. to −88° C. for the purpose of killing tissue in surgical procedures. Liquid nitrogen has also been used as a refrigerant in probes. This refrigerant has a boiling point at atmospheric pressure of −196° C. Some probes provide very small cold surfaces for surgical procedures in the eye, brain or heart, and other probes require larger surface areas, and more cooling power for operation on larger tissue volumes and areas.

These cryo-probes generally have at least two circuits, one for delivering refrigerant to the active or distal end of the probe where cryosurgery is performed, and the other circuit for returning refrigerant from the active cold end to a vent port. The refrigerant generally is a superheated vapor at discharge. Probes of the prior art differ from each other generally in the means that are employed to keep the outside surfaces of the cryo-probe warm, except for the active end, and in the means for warming the cryo-probe after the surgical procedure is completed. Rapid warming is especially important when an ice ball forms on the cold working end of the probe during surgery, and it is not possible to safely move or remove the probe until the probe is separated from the ice ball or the ball is melted.

It is desirable that the apparatus, i.e., the refrigerant supply and control system for a cryo-probe be located outside the sterile field where cryosurgery is performed. Accordingly, conduits of extended length are required between the control and supply apparatus and the probe itself. It is also desired that any vented refrigerant be disposed outside of the sterile field. These logistical matters must be accommodated with the least inconvenience and impediment to the surgeon. Thus, long, flexible and small gauge conduits are desirable between the supply and the probe.

Efficient use of refrigerant is also important so that local supplies of refrigerant are not quickly exhausted, and the need to complete surgery quickly because of limitations and availability of refrigerant, is eliminated as a major consideration for the surgeon.

In summary, what is needed is a cryo-probe of high performance capability that is easy and convenient for a surgeon to use during surgery.

SUMMARY OF THE INVENTION

An object of the present invention is to provide an improved cryo-probe that provides rapid warming of the probe tip after a surgical procedure, or step in a procedure, is completed.

Another object of the invention is to provide an improved cryo-probe that utilizes refrigerant stored at or near room temperature so that supply lines need not be insulated.

Still another object of the invention is to provide an improved cryo-probe with rapid warm-up, and delivery of cold fluid to the operating tip in a pre-cooled state so as to improve operating efficiency.

In the cryo-probe in accordance with the invention, refrigerant is furnished from a high pressure gas supply that is maintained at room temperature. Thus, insulation of the lines delivering refrigerant to the probe is unnecessary. Refrigerant from the supply flows through a pre-cooling heat exchanger in the probe and then through a capillary tube wherein the pressure drops. In accordance with the Joule-Thompson effect, the refrigerant expands and becomes cold. A portion of the incoming refrigerant may condense to liquid during the Joule-Thompson expansion and this two-phase mixture of gas and liquid is applied in the region of the cryo-tip to provide rapid cooling thereof.

The expanded refrigerant gas at low pressure reverses direction and flows back from the cold tip in counterflow arrangement through the aforementioned heat exchanger to give a pre-cooling effect to the refrigerant incoming from the external supply. The heat exchanger with its pre-cooling effect increases the cooling (heat-absorbing) capacity of the mass flow of refrigerant. Thus, efficiency of the probe is improved.

A second tube for conveying warm-up gas is located in the probe and extends to the cold tip. After cryosurgery is complete, warm gas is delivered to the tip in the probe at reduced pressure from the same refrigerant supply as is used for cooling. However, Joule-Thompson expansion of the gas is not provided in the probe for this warm-up flow. Accordingly the tip is warmed by the low pressure refrigerant and any ice ball that is formed during surgery may be defrosted and melted rapidly.

The invention accordingly comprises the features of construction, combinations of elements, and arrangements of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a side elevational view, in cross-section, of a cryo-probe in accordance with the invention;

FIG. 2 is a side elevational view in cross-section, of an alternative embodiment of a cryo-probe in accordance with the invention;

FIGS. 3, 4 and 5 are sectional views taken along the lines 3—3, 4—4, and 5—5 respectively, of FIG. 2;

DESCRIPTION OF THE PREFERRED EMBODIMENTS

Figure 6:
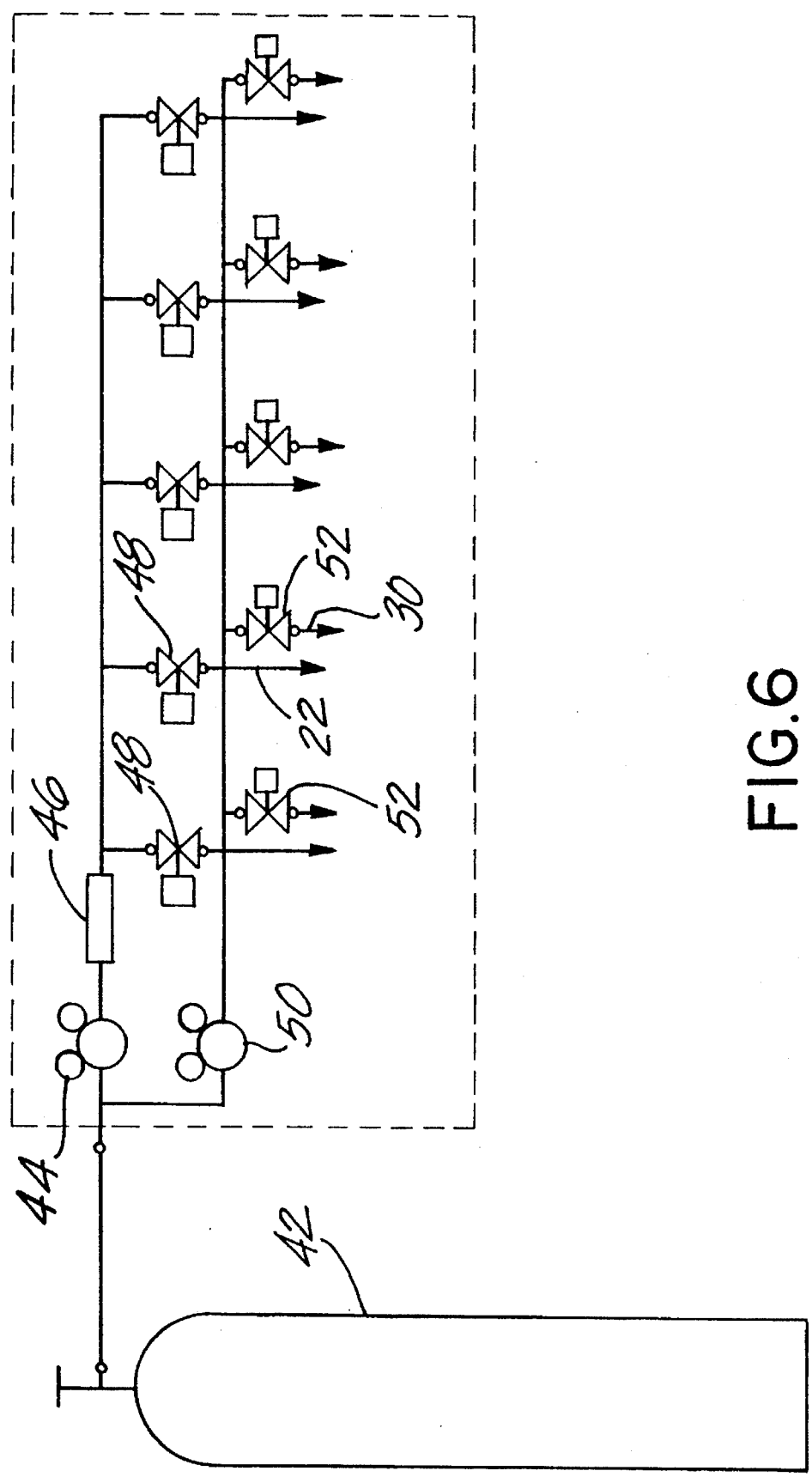
FIG. 6 is a schematic diagram of a gas supply system for cryo-probes in accordance with the invention.

With reference to FIG. 1, a cryo-probe 10 in accordance with the invention includes a thin walled metal tube 12 having a cold distal end 14 and a warm proximal end 16 to which a long plastic tube 18 is attached. A matrix tube type heat exchanger 20 is located within the metal tube 12 near the cold end 14. A high pressure gas inlet tube 22 extends from the warm end 16 into the tube 12 and connects at its end 24 to the heat exchanger 20 so that high pressure gas, in use, may be delivered to the heat exchanger 20 for pre-cooling, as discussed hereinafter. From the heat exchanger 20, the refrigerant gas enters the cold zone 26 of the cryo-probe 10 and flows through a capillary tube 28 of small internal diameter from which it is discharged near the distal end 14 of the probe 10. The expansion in the capillary tube 28 is substantially isenthalpic.

The capillary tube 28 is wrapped around a hollow mandrel 30 that also serves as a warm-up gas inlet. Refrigerant leaving the capillary tube 28 at lowered pressure is cold and chills the cold end 14 of the metal tube 12 within the cold zone 26. A spacer sleeve 32 surrounds the capillary tube 28 in the cold zone 26 so that heat transfer from the metal tube 12 in the cold zone to the refrigerant is enhanced by forcing the refrigerant to flow at a higher velocity. The refrigerant flows back outside the spacer sleeve 32 toward the matrix tube heat exchanger 20. There, the return gas cools the gas entering the heat exchanger through the high pressure gas inlet tube 22, 24.

In the heat exchanger 20, the expanded low pressure return gas flows through an annular region in heat exchange relationship with the incoming gas delivered by the tube 22, 24. The annular region is filled with a porous material, e.g., a metal screen, through which the gas flows to enhance heat transfer. The screen is in thermodynamic contact with the heat exchanger tubing that connects with the refrigerant inlet tube 22. Such a screen construction improves heat transfer and is disclosed in U.S. Pat. No. 4,781,033, which is incorporated herein by reference. The now superheated gas then flows (arrow 31) toward the warm end 16 and into the plastic tube 18. Ultimately, the gas leaving the probe is discharged into the ambient air or is collected for recycling.

In operation, a high pressure refrigerant gas is delivered to the inlet tube 22 at the warm end 16 of the cryo-probe 10. The high pressure gas flows through the matrix heat exchanger 20 where it is pre-cooled. The gas then flows to the capillary tube 28 where the restriction of the small tube causes the pressure to drop and in accordance with the Joule-Thompson effect, the gas temperature falls. Some of the gas may be condensed to a liquid as it flows through the capillary tube 28. The refrigerant, liquid and/or gas, leaves the capillary tube 28 within the cold end 14 of the probe 10 and cools the outer sleeve 12 at that location. Cooling extends, in a short time, through the entire cold zone 26. A temperature sensor 34, located near the discharge end of the capillary tube 28, verifies performance of the system in providing cold temperatures. This signal may also be used for refrigerant control purposes.

The low pressure expanded gas, having been warmed in cooling the cold zone 26, but nevertheless colder than the high pressure incoming gas at the inlet 24 to the heat exchanger 20, flows back through the exchanger 20 in counterflow with the incoming gas and thereby provides the aforementioned pre-cooling. The gas, now superheated, flows 31 within the metal sleeve 12 to the plastic tube 18, and then out of the sterile zone where surgery is performed.

As is known in cryosurgery, a ball of water may freeze around the distal end 14 of the cryo-probe 10 as cells are frozen and destroyed. It is necessary that the probe be disengaged from the ice ball so that the probe may be withdrawn from or moved within the surgical site. Whereas the probe will release from the ice ball in time after supply of the high pressure refrigerant gas is terminated, it is desirable that the probe be removed, or moved from one place to another, as soon as possible. Accordingly, an active warm-up procedure that separates the probe from the ice ball is desirable.

In FIG. 1, the mandrel 30 that extends from the warm end 16 and out (to the left in FIG. 1) to the gas supply is used to deliver low pressure gas from the gas supply directly to the distal or cold end 14 of the probe 10.

This low pressure, warm gas is not put through a capillary tube and thus there is no Joule-Thompson effect within the probe. The low pressure gas circulates within the cold zone 26 and flows back 31 through the same channels that the coolant gas followed in its return from the cold zone 26 to discharge outside the warm end 16 of the probe 10. Low pressure gas is provided through the warm-up tube or mandrel 30 only when high pressure gas is cut off from flow through the cooling circuit 22, 20, 28 to the cold zone (and vice versa). The temperature sensor 34 gives indication of the effectiveness of the warm-up gas.

FIG. 2 illustrates an alternative embodiment of a cryo-probe 10' in accordance with the invention. The probe construction of FIG. 2 and its performance are substantially similar to that of FIG. 1. Accordingly, the same reference numerals are used to identify common parts.

The embodiment of FIG. 2 utilizes a heat exchanger 33 that is comprised of circular cross-section tubing 35 having external fins. The finned tubing 35 is wound about the mandrel 30 and fills the annulus between the mandrel 30 and the inner surface of the metal tube or sleeve 12. This arrangement may be characterized as a crossflow/counter-flow heat exchanger, with the high pressure gas flowing within the tubing and the low pressure gas flowing over the outer finned surface of the tubing.

A second temperature sensor 36, located in the return passage at the entrance to the heat exchanger 33, gives an indication of the effectiveness of the warm-up gas during the warm-up procedures. The sensor 36 also provides an indication of the degree to which the returning gas is super-heated during the cooling, cryosurgical procedure.

FIGS. 3, 4 and 5, are cross-sections of the probe 10' indicating the relative positions of the gas supply line 22, warm-up tube 30, finned tubing 35 and external sleeve 12. Electrical leads 38 for the sensors 34, 36 are located within the warm-up tube 30. Return gas occupies all of the space 40 not filled by the heat exchanger 33, tubes, etc.

FIG. 6 schematically illustrates a gas supply system for use with the probes 10, 10' in accordance with the invention. The system includes a high pressure gas bottle 42, which delivers gas through a pressure regulator 44, through an adsorber 46 for removal of foreign matter and moisture to a start-stop solenoid valve 48 having an output that connects to the high pressure gas inlet tube 22 in the cryo-probes 10, 10'. The system of FIG. 6 allows for independent operation of five cryo-probes in parallel, or one at a time or in any combination.

From the same tank 42, gas is fed through a second pressure regulator 50 to an on-off solenoid valve 52. The output of the valve 52 connects to the input of the warm-up tube, i.e., the hollow mandrel 30. Warm or high pressure gas can be supplied to individual cryo-probes independently of each other. The return path for the "exhausted" refrigerant is not shown in FIG. 6. A refrigerant suitable for use in probes as discussed in relation to FIGS. 1 and 2 may be argon stored at room temperature in a gas bottle 42 at 6,000 pounds per square inch pressure. The warm-up gas may be delivered to the probe at a reduced pressure of approximately 100 psi. In passing through the regulator 50, the gas becomes chilled. However, in flowing through the plastic tubing 18, heat is absorbed from the ambient and the gas reaches the probe at near room temperature. With different refrigerants, pressures, etc., a small heater (not shown) may be required between the regulator 50 and the cryo-probe to assure rapid warm up.

Using Argon, the capillary tube 28 may be, e.g., approximately 300 mm long and have an inside diameter of approximately 0.2 mm, although no limits can be set. The physical requirements differ with the anticipated heat load, desired cold temperature, selection of refrigerant, etc.

Figure 7:
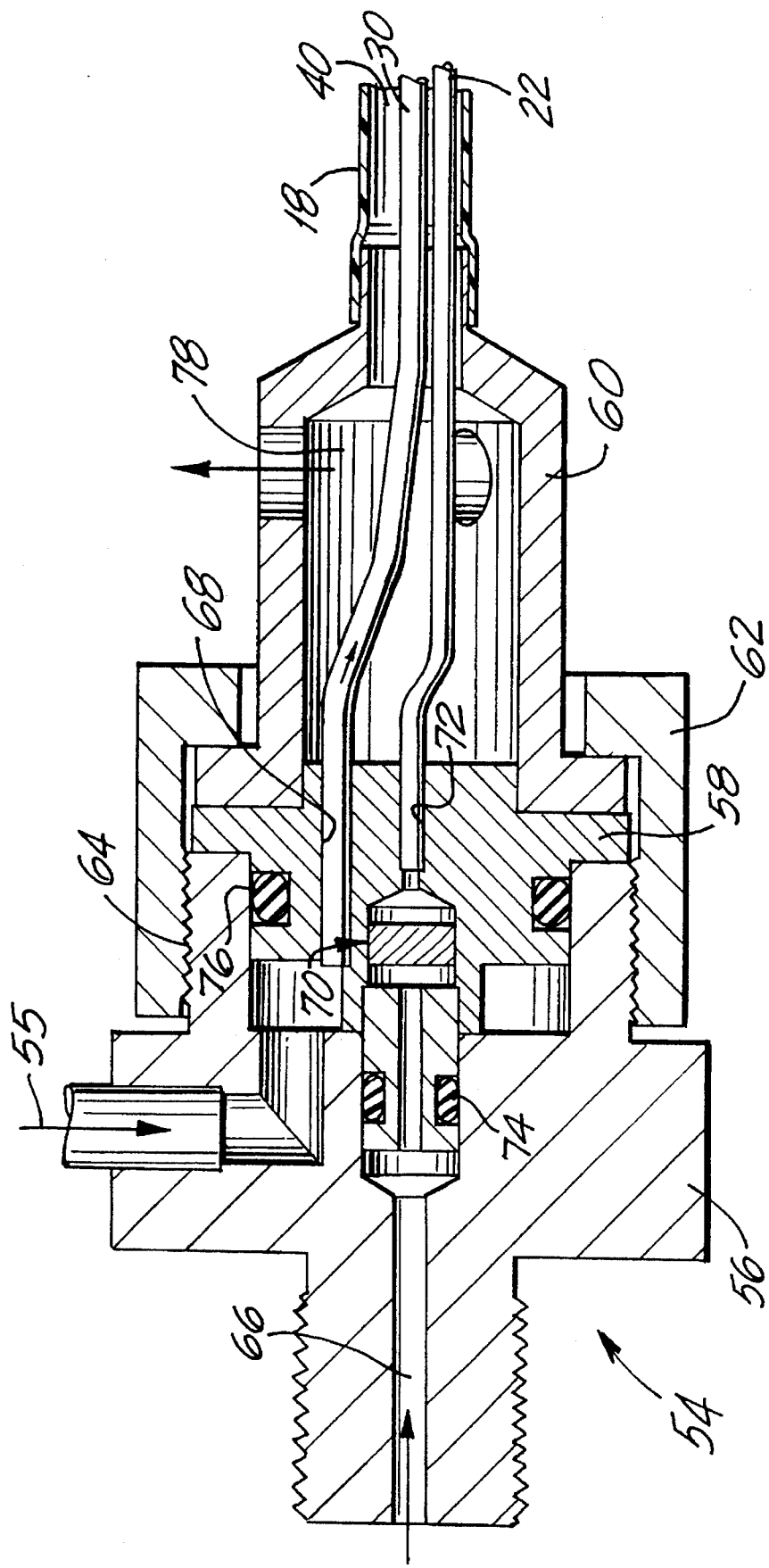
FIG. 7 is an enlarged view in cross-section of a gas coupling for use with cryo-probes in accordance with the invention.

FIG. 7 illustrates details of a concentric gas coupling 54 as may be used at the warm end 16 of the probe 10. A nut 62 that threadably engages external threads 64 on a body 56, rigidly connects the body 56 to a core 58 and nipple 60. Warm gas 55 at an elevated pressure, e.g., 100 psi, enters the body 56 transversely to the longitudinal axis 66 of the coupling 54, being connected in use to one of the valves 52 (FIG. 6). The warm gas flows from the body 56, through an opening 68 in the core 58 and then into the hollow mandrel 30 that extends the length of the cryo-probe 10, 10'.

High pressure gas, e.g., at 6,000 psi from a valve 48 (FIG. 6), enters the body 56 axially and passes through a filter 70 which removes foreign matter so as to protect the capillary tube 28 (FIG. 1) from clogging downstream in the cryo-probe 10, 10'. The high pressure gas flows through a channel 72 in the core 58 where the gas enters the high pressure gas inlet tube 22 that extends to the cold end 14 of the probe 10, 10'. An O-ring 74 between the filter 70 and body 56 prevents out-leakage of the high pressure gas, and an O-ring 76 prevents out-leakage of the warm-up gas at a lower pressure from between the core 58 and body 56. Thus, there is no out-leakage of either the high pressure or low pressure gas from the coupling 54.

By loosening the nut 62, the transverse inlet for the warm-up gas 55 can be set at any angular orientation relative to the axis 66 before the nut 62 is retightened. Thus, the connections between the supply and probe can be relieved of twisting stresses which may bother the surgeon. A vent hole 78 allows return from the cold end 16 and discharge to the atmosphere, of both the cooling gas and the warm-up gas, in turn.

To simplify assembly and servicing of the device, the core 58 may be permanently brazed to the nipple 60, and the tubing 22 and filter 74 may also be attached to the core 58 by brazing.

Although a capillary tube has been illustrated and described above as the flow restrictor between the high pressure and low pressure regions of the probe, it should be understood that in alternative embodiments of the invention, other flow restrictors may be used, e.g., a simple orifice (not shown) at the cold end of the high pressure refrigerant delivery tube proximate the cold end of the probe.

Figure 8:
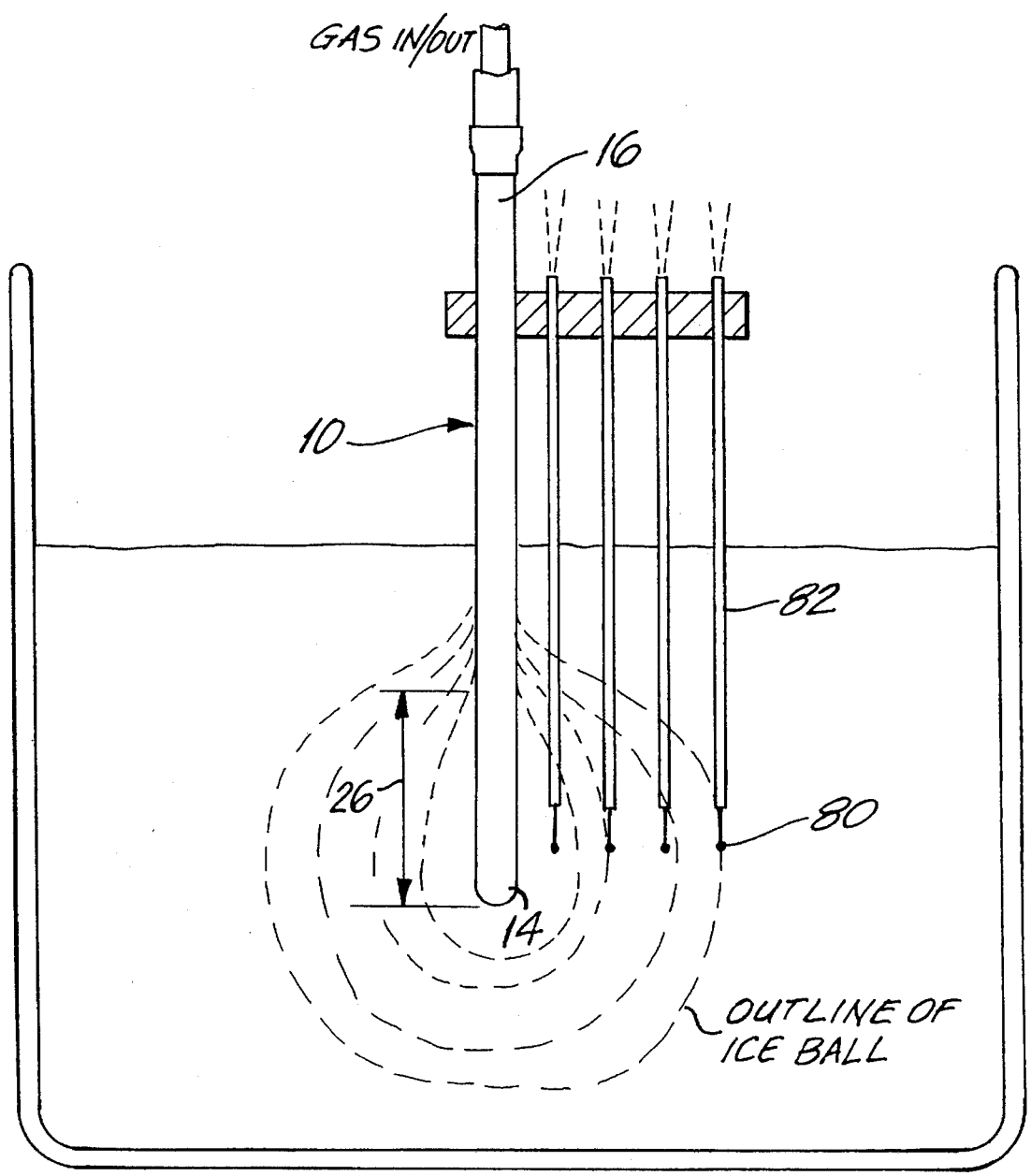
FIG. 8 illustrates an experimental apparatus for measurement of temperature gradients around the tip of a cryo-probe in accordance with the invention.

FIG. 8 illustrates a test facility for evaluating performance of the probe 10, 10' in accordance with the invention. The probe 10 is vertically inserted in a test medium, e.g., beef liver, and temperature sensors are connected to rods 82 so that a distribution of temperatures radially outward of the probe 10 may be measured, e.g., at radial distances of 0.5, 1.0, 1.5 and 2.0 cm.

Figure 9:
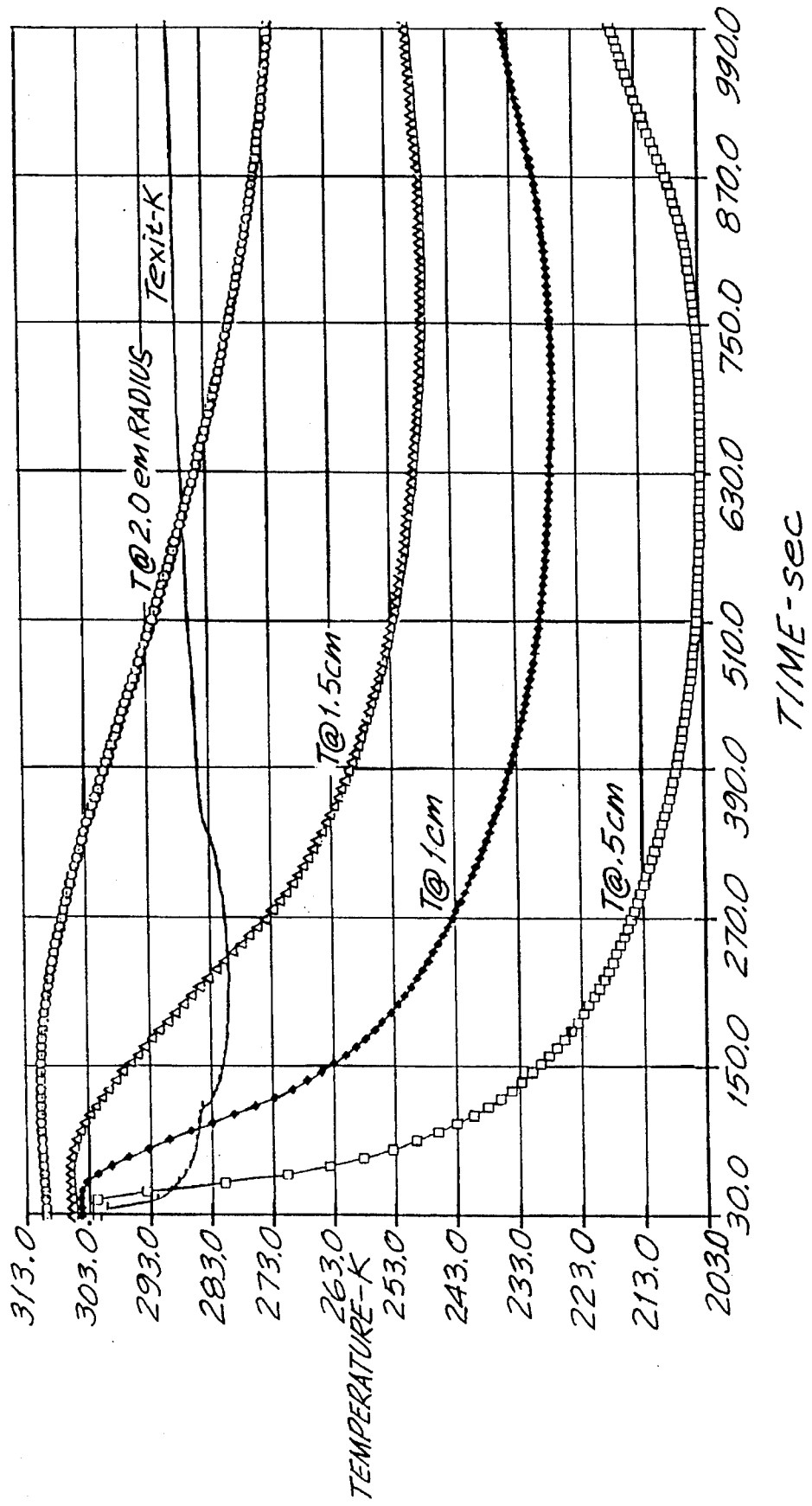
FIG. 9 is a chart of temperature versus time indicating performance of a cryo-probe in accordance with the invention as measured by the apparatus of FIG. 8.

FIG. 9 presents the temperature-time characteristics of a probe 10 in accordance with the invention as determined using the test facility of FIG. 8, and using argon gas as a refrigerant. It should be noted that water and tissue freeze at 273K. During the test the cold zone 26 was at approximately 120K and the tissue was in a bath at 303K.

Efficiency of the probes 10, 10' may be improved by using a rubber or plastic material, rigid or resilient, of low thermal conductivity for the outer sleeve 12 except for the cold zone 26 where a high conductivity metal is always desired. This construction will greatly reduce unwanted heat flow by conduction along the tube 12 to the cold zone and thereby increase efficiency and reduce response time in cooling. Differences in thermal expansion coefficients of materials, sterilization requirements, etc., must be taken into account when constructing such a hybrid probe enclosure.

Further, the inside hemispherical surface of the tube 12 at the cold end 14 may have its surface area 84 increased by the addition of internal fins, ridges, etc., to improve heat transfer (FIG. 2). Additionally, or alternatively, the hemispherical internal space may be filled with a porous, highly conductive material, such as, e.g., steel wool or a sintered metal core that improves heat transfer without blocking the flow of refrigerant.

It will thus be seen that the objects set forth above, and those made apparent from the preceding description, are efficiently attained, and, since certain changes may be made in the above constructions without departing from the spirit or the scope of the invention, it is intended that all matter contained in the above description, and shown in the accompanying drawings, shall be interpreted as illustrative and not in a limiting sense.

What is claimed is:

1. A cryo-probe for applying low temperatures to destroy tissue cells in surgery, comprising:

a hollow sleeve of extended length having a closed end and an open end;

a first inlet tube having a first end and a second end and being extended longitudinally within said sleeve, said first inlet tube being for connection to a refrigerant supply at said first end of said first inlet tube;

a second inlet tube extending longitudinally within said sleeve and terminating proximate said closed end of said sleeve, said second inlet tube being for connection to a supply of warming medium;

a heat exchanger within said sleeve and having a high pressure path and a low pressure path for transferring heat between two flows of refrigerant respectively in said paths, said second end of said first inlet tube connecting to one end of said high pressure heat exchanger path, said heat exchanger being mounted coaxially around said second inlet tube;

a flow restrictor having an input connected to the other end of said high pressure heat exchanger path and an outlet proximate said closed end of said sleeve, a cold tip being formed in said sleeve between the closed end of said sleeve and the inlet end of said low pressure heat exchanger path, a discharge end of said low pressure heat exchanger path being directed toward a vent.

2. A cryo-probe as in claim 1, wherein said restrictor is a capillary tube wound around said second inlet tube and positioned between said heat exchanger and said cold tip.

3. A cryo-probe as in claim 2, wherein said capillary tube is encased in a spacer tube, an annular flow passage being formed between said spacer tube and said hollow sleeve.

4. A cryo-probe as in claim 1, wherein said heat exchanger is one of a matrix tube type and a finned tube type.

5. A cryo-probe as in claim 1, further comprising at least one temperature sensor in said sleeve, said at least one temperature sensor being located at at least one of said cold tip and said inlet to said low pressure heat exchanger path.

6. A cryo-probe for applying low temperatures to destroy tissue cells in surgery, comprising:

a hollow sleeve of extended length having a closed end and an open end;

a first inlet tube having first and second ends and extending longitudinally within said sleeve, said first inlet tube being for connection to a refrigerant supply at said first end of said first inlet tube;

a second inlet tube extending longitudinally within said sleeve and terminating proximate said closed end of said sleeve, said second inlet tube being for connection to a supply of warming medium;

a heat exchanger within said sleeve and having a high pressure path and a low pressure path for transferring heat between two flows of refrigerant respectively in said paths, said heat exchanger encircling a first portion of said second inlet tube, said second end of said first inlet tube connecting to one end of said high pressure heat exchanger path;

a capillary tube flow restrictor encircling a second portion of said second inlet tube between said heat exchanger and said cold tip, the end other end of said high pressure heat exchanger path connecting to an inlet end of said capillary tube, an outlet end of said capillary tube being proximate said closed end of said sleeve, in operation, refrigerant applied to said first inlet tube flows through said high pressure side of said heat exchanger, through said capillary tube where pressure drops, volume expands and temperature drops, then refrigerant flows to said cold tip at the discharge of said capillary tube and from said cold tip through said low pressure path of said heat exchanger and back toward said open end of said sleeve.

7. A cryo-probe as in claim 6, wherein said second inlet tube is coaxially concentric with said sleeve, and said heat exchanger fills an annular space between said sleeve and said second inlet tube.

8. A cryo-probe as in claim 6, further comprising a spacer tube surrounding said capillary.

9. A cryo-probe as in claim 6, wherein the total flow cross-section of said first and second inlet tubes is less than the internal cross-section area of said sleeve, whereby gas leaving said low pressure heat exchanger path fills the space around said inlet tubes, said space connecting to the open end of said sleeve and said vent.

10. A cryo-probe as in claim 6, further comprising said supply of refrigerant, said supply being connected to said first inlet tube for delivery of refrigerant thereto at a first pressure, and said supply being connected to said second inlet tube for delivery of refrigerant thereto at a second pressure, said first pressure being greater than said second pressure, and flow blocking means for preventing back flow of refrigerant discharged from said capillary tube through said second tube and toward said open end of said sleeve.

11. A cryo-probe as in claim 10, wherein said supply is at room temperature.

12. A cryo-probe as in claim 6, wherein the inner surface of said cold tip at the closed end of said sleeve includes means for extending the thermodynamic surface at said cold tip, whereby heat transfer is enhanced.

13. A cryo-probe as in claim 12, wherein said surface extender means includes at least one of ridges, fins, and porous conductive material.

14. A cryo-probe as in claim 1, wherein at least said closed end of said sleeve is fabricated of highly thermally conductive material.

* * * * *